United States Patent [19]

Rule

[11] Patent Number: 4,788,336

[45] Date of Patent: Nov. 29, 1988

[54] NOVEL ORGANIC COMPOUNDS FOR USE IN ELECTROPHOTOGRAPHIC ELEMENTS

[75] Inventor: Norman G. Rule, Rochester, N.Y.

[73] Assignee: Eastman Kodak Company, Rochester, N.Y.

[21] Appl. No.: 6,400

[22] Filed: Jan. 23, 1987

[51] Int. Cl.[4] .............................................. C07C 87/50

[52] U.S. Cl. .................................... 564/315; 564/330; 564/433; 430/73; 430/74

[58] Field of Search .................... 430/73, 74; 564/315, 564/316, 330, 433

[56] References Cited

U.S. PATENT DOCUMENTS

| | | | |
|---|---|---|---|
| 3,234,280 | 2/1966 | Fox et al. | 564/433 |
| 3,542,544 | 11/1970 | Seus et al. | 430/73 |
| 3,615,402 | 10/1971 | Rule | 430/73 |
| 3,820,989 | 6/1974 | Rule et al. | 430/73 |
| 4,025,341 | 5/1977 | Rule | 430/73 |
| 4,127,412 | 11/1978 | Rule et al. | 430/73 |
| 4,140,529 | 2/1979 | Pai et al. | 430/71 |
| 4,360,660 | 11/1982 | Watarai et al. | 528/266 |

FOREIGN PATENT DOCUMENTS

| | | |
|---|---|---|
| 0753415 | 7/1970 | Belgium . |
| 0052961 | 6/1982 | European Pat. Off. . |

*Primary Examiner*—J. David Welsh

*Attorney, Agent, or Firm*—Richard D. Fuerle

[57] ABSTRACT

In accordance with the present invention there is provided an organic compound having the formula selected from the group consisting of:

(a)

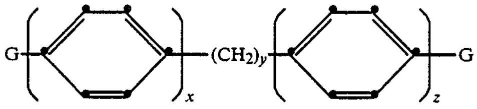

wherein x is an integer from 0 to 2, y is an integer from 1 to 6, and z is an integer from 0 to 2;

(b)

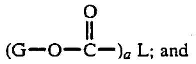

and (c)

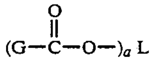

wherein L is aliphatic, alicyclic or aromatic and a is an integer from 2 to 6; and wherein G has the formula

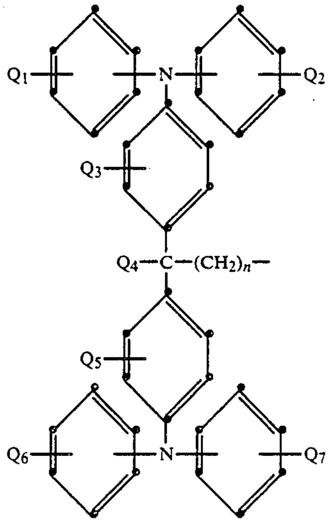

wherein n is an integer from 0 to 6 and $Q_1$, $Q_2$, $Q_3$, $Q_5$, $Q_6$, and $Q_7$, which may be the same or different, represent H or $CH_3$, and $Q_4$ represents H or $CH_3$ when x and z are 0 or n is greater than 0, or $Q_4$ represents $CH_3$ when x or z are 1 or 2 and n is 0.

The compounds, which exhibit unexpectedly high $T_g$ and unexpectedly high resistance to oxidation, are useful in electrophotographic elements.

8 Claims, 3 Drawing Sheets

NOVEL ORGANIC COMPOUNDS FOR USE IN ELECTROPHOTOGRAPHIC ELEMENTS

FIELD OF THE INVENTION

This invention relates to electrophotography and, more specifically, to organic compounds useful in electrophotographic elements.

BACKGROUND OF THE INVENTION

The process of electrophotography as disclosed by Carlson in U.S. Pat. No. 2,297,691, employs an electrophotographic element comprising a support material bearing a coating of an insulating material whose electrical resistance varies with the amount of incident electromagnetic radiation it receives during an imagewise exposure. The element, commonly termed an electrophotographic element, is first given a uniform surface charge in the dark after a suitable period of dark adaptation. It is then exposed to a pattern of actinic radiation which has the effect of differentially reducing the potential of this surface charge in accordance with the relative energy contained in various parts of the radiation pattern.

The differential surface charge, or electrostatic latent image, remaining on the electrophotographic element is then developed by contacting the surface with a suitable electroscopic marking material. Such marking material, or toner, whether contained in an insulating liquid or in a dry developer, is deposited on the exposed surface in accordance with either the charge pattern or discharge pattern depending on the charge polarity of the toner and the surface of the element. Deposited marking material is either permanently fixed to the surface of the electrophotographic element by means such as heat, pressure, or solvent vapor, or transferred to a receiver element to which it is similarly fixed. Likewise, the electrostatic charge pattern can be transferred to a receiver element and developed there.

There are a variety of different configurations for electrophotographic elements. An electrophotographic element may comprise a homogeneous photoconductive layer, it may comprise an aggregate layer containing a photoconductor and a sensitizing dye, or it may be a composite or multilayer element.

An example of an electrophotographic element comprising a single homogeneous photoconductive layer is one having a film-forming polymeric organic photoconductor and sensitizing dye coated on an electrically conductive substrate. In such an element the sensitizing dye and the organic photoconductor are dissolved uniformly through the photoconductive layer and no heterogeneity can be seen under high magnification.

Electrophotographic elements comprising aggregate layers typically comprise an electrically conductive substrate, which is coated with sensitizing dye dispersed in a polymeric binder. In these elements the dye and some of the polymer combine (aggregate) together to form a crystal-like complex which is visible under magnification and is randomly distributed through the photoconductive layer.

Multilayer or composite electrophotographic elements typically comprise three layers. The first being an electrically conductive substrate coated with a charge-generation layer upon which is coated a charge-transport layer. Generally in elements of this type the charge-transport layer, containing no sensitizer (i.e. no charge-generation material) is homogeneous under high magnification. The charge-generation layer is coated as a thin separate layer underneath the charge-transport layer. Charge-transport material is often added to this charge-generation layer. Next, in turn, is the conductive layer. Examples of these three types of electrophotographic elements are well known in the art.

U.S. Pat. No. 4,140,529 discloses a photoconductive element having a charge-transport overlayer. The charge-transport layer comprises an organic resinous material comprising from about 10 to about 75% by weight of:

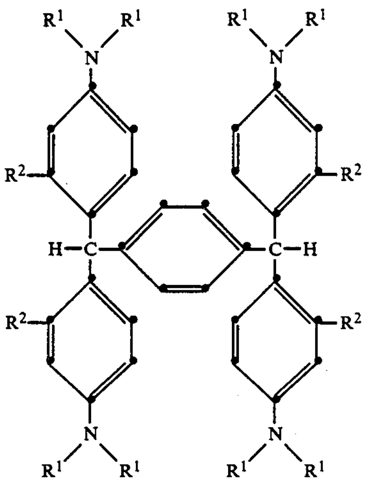

where $R^1$ is selected from the group consisting of an alkyl with from 1 to 12 carbon atoms and an alkyl with from 1 to 12 carbon atoms substituted by aryl groups selected from the group consisting of phenyl, naphthyl, anthryl, and biphenyl and $R^2$ is selected from the group consisting of methyl, ethyl, chloro, bromo and hydrogen. It was further disclosed that transport layers comprising the above material were found to have a high glass transition temperature ($T_g$). It was also stated that the material retained its electrical properties after extensive cycling and exposure to the environment, i.e. oxygen, ultraviolet radiation, elevated temperatures, etc.

Belgian Pat. No. 753,415 discloses a photoconductive composition for use in electrophotographic elements. The photoconductive composition comprises substituted xylylidene of the general formula:

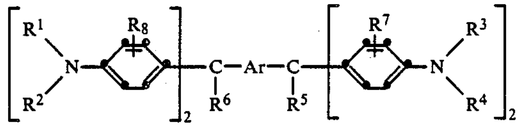

wherein $R^1$, $R^2$, $R^3$ and $R^4$ represent an alkyl or substituted alkyl group, an aryl or substituted aryl group, $R^5$ and $R^6$ represent a hydrogen or hydroxy group, Ar represents a phenylene or substituted phenylene group, and $R^7$ and $R^8$ represent a substituted or unsubstituted alkyl group, a substituted or unsubstituted aryl group or hydrogen.

It is disclosed that "elements containing these photoconductors are markedly stable to oxidation and have good shelf life even at elevated temperatures compared to many other photoconductive compounds".

However, there is a need for electrophotographic elements which possess a high $T_g$ and at the same time are resistant to oxidation. High Tg is desirable, for example, when an element is used in a thermal transfer process comprising the direct thermal transfer of a toner image from a reusable electrophotographic element to a plain paper receiver. In such a process, toner is applied directly to the surface of the electrophotographic element, the receiver is positioned directly thereover and the sandwich is heated. It is necessary that the toner fully adhere to the receiver and then strip cleanly away from the element without damaging the element surface. This operation is achieved more readily if, despite the high temperature used, the element remains in a glassy state rather than transforming to a rubbery state, i.e., the element is operating below its $T_g$. In addition it is important that the materials used in electrophotographic elements be resistant to oxidation and not form a dye derivative which causes undesirable coloration and/or affects spectral sensitivity.

SUMMARY OF THE INVENTION

In accordance with the present invention there is provided an organic compound having the formula selected from the group consisting of:

(a)

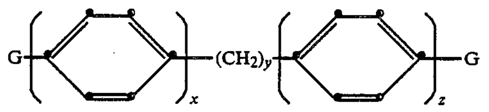

wherein x is an integer from 0 to 2, y is an integer from 1 to 6, and z is an integer from 0 to 2;

(b)

$$(G-O-\overset{O}{\overset{\|}{C}}-)_a\,L;\ \text{and}$$

(c)

$$(G-\overset{O}{\overset{\|}{C}}-O-)_a\,L$$

wherein L is aliphatic, alicyclic or aromatic and a is an integer from 2 to 6; and wherein G has the formula

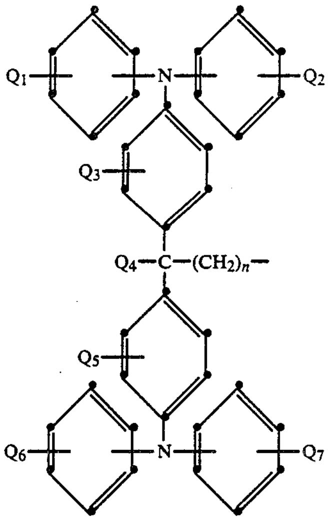

wherein n is an integer from 0 to 6 and $Q_1$, $Q_2$, $Q_3$, $Q_5$, $Q_6$, and $Q_7$, which may be the same or different, represent H or $CH_3$, and $Q_4$ represents H or $CH_3$ when x and z are 0 or n is greater than 0, or $Q_4$ represents $CH_3$ when x or z are 1 or 2 and n is 0.

The compounds of the present invention, described above, will hereinafter be referred to as "cluster triarylamines". In accordance with an especially useful embodiment of the present invention, electrophotographic elements are provided exhibiting unexpected increases in thermal stability. This highly beneficial result is obtained by incorporating in such electrophotographic elements one or more of the cluster triarylamines described above. It has been found that these cluster triarylamines exhibit an unexpectedly high glass transition temperature (Tg), (i.e. in excess of 90° C.) and an unexpectedly high resistance to oxidation.

In one embodiment in accordance with the present invention, one or more of the cluster triarylamines described above are employed in a continuous polymer phase of a multiphase aggregate photoconductive composition. An example of an aggregate photoconductive composition (as it is referred to hereinafter) is the subject matter of U.S. Pat. No. 3,615,414 issued Oct. 26, 1971 to William A. Light and assigned to Eastman Kodak Company.

In another embodiment in accordance with the invention, one or more of the cluster triarylamines described above is employed in a homogeneous organic electrophotographic element, for example, an electrically conductive substrate having thereon a homogeneous organic photoconductive composition comprising a solid solution of one or more cluster triarylamines and a polymeric binder.

In yet another embodiment in accordance with the invention, one or more of the cluster triarylamines is employed to form one or more layers of a multilayer electrophotographic element. In such multilayer elements one layer functions as a charge-generation layer while a second layer functions as a transport layer for the generated charge. Cluster triarylamines may be used in either the charge-transport layer or as an addendum in the charge-generation layer.

The electrophotographic elements of the present invention have substantially improved resistance to oxidation. In addition, it has been found that the cluster triarylamines of the present invention enhance the thermal stability of electrophotographic elements. This combination of thermal stability and oxidation resistance is not found in prior art elements.

DETAILED DESCRIPTION

Figure 1:
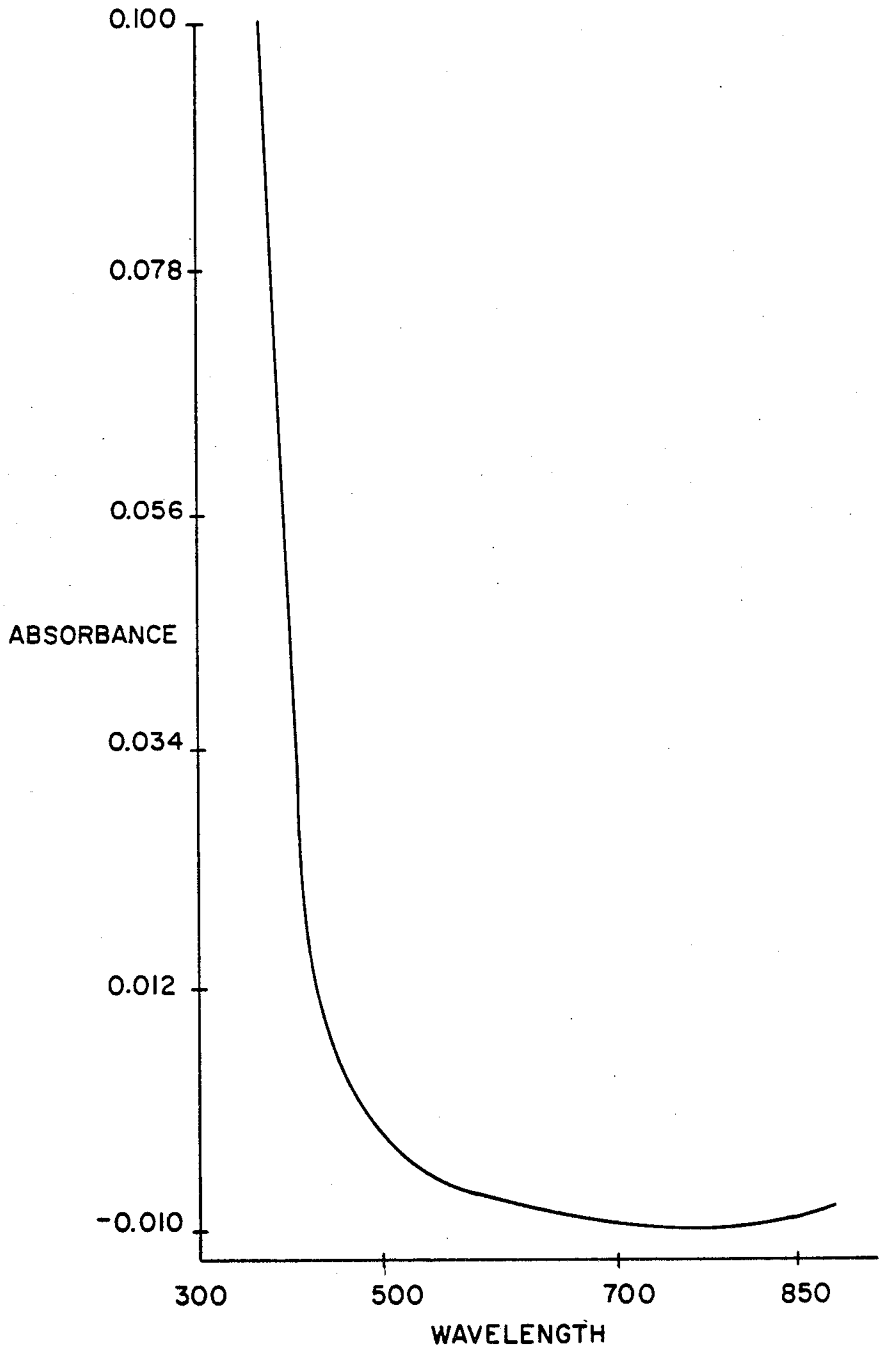
FIG. 1 is an absorption curve for a compound of the present invention which has been subjected to an accelerated oxidation test.

The organic compounds of this invention may be characterized by the following formulas:

(a)

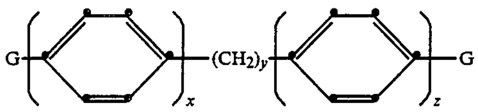

wherein x is an integer from 0 to 2, y is an integer from 1 to 6, and z is an integer from 0 to 2;

(b)

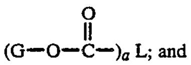

(c)

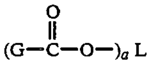

wherein L is aliphatic, alicyclic or aromatic and a is an integer from 2 to 6; and wherein G has the formula

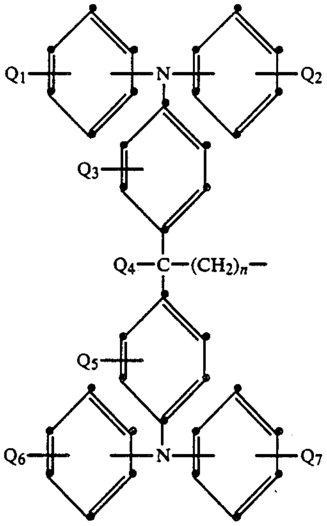

wherein n is an integer from 0 to 6 and $Q_1$, $Q_2$, $Q_3$, $Q_5$, $Q_6$, and $Q_7$, which may be the same or different, represent H or $CH_3$, and $Q_4$ represents H or $CH_3$ when x and z are 0 or n is greater than 0, or $Q_4$ represents $CH_3$ when x or z are 1 or 2 and n is 0.

The structures of representative organic compounds as described herein are shown in Table I below:

TABLE I

I.

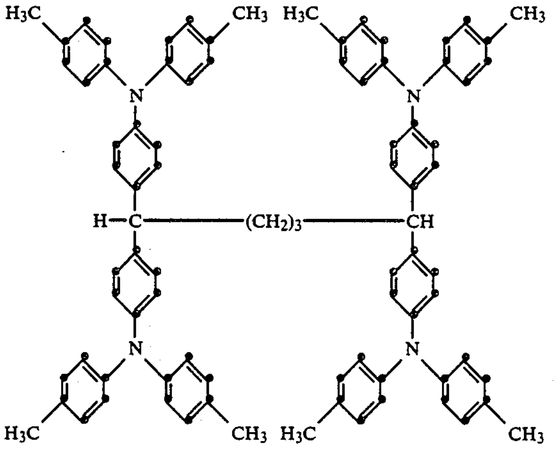

TABLE I-continued
II.
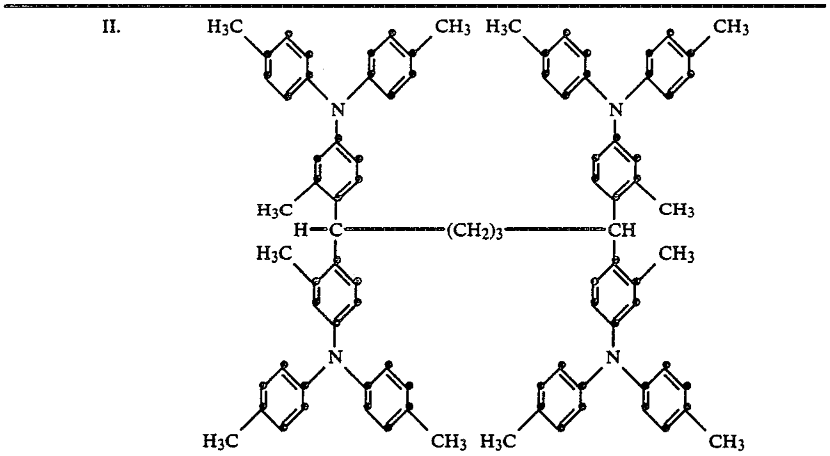
III.
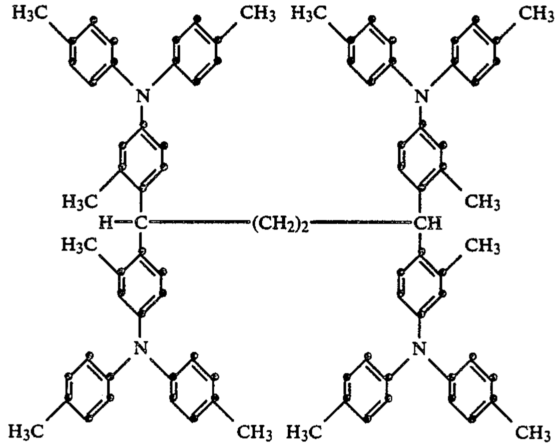
IV.
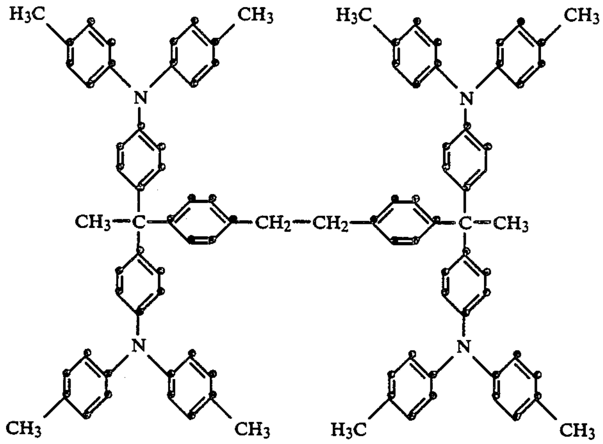
V.
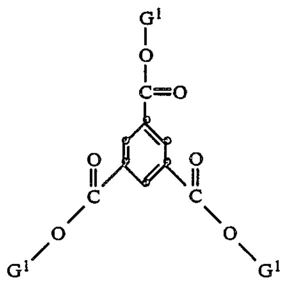

TABLE I-continued
where $G^1$ =
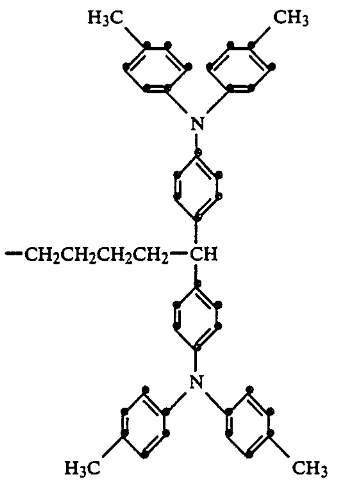
VI.
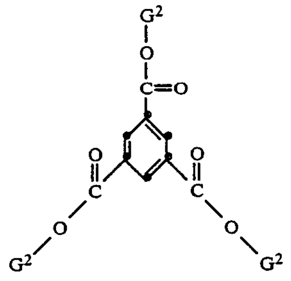
where $G^2$ =
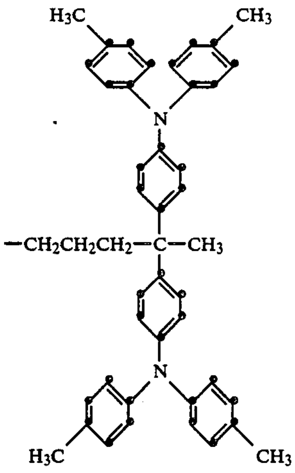
VII.
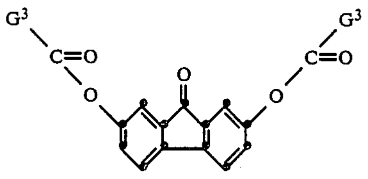
VIII.
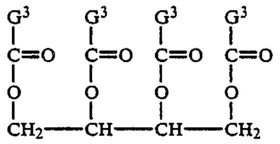

TABLE I-continued

| | |
|---|---|
| IX. | 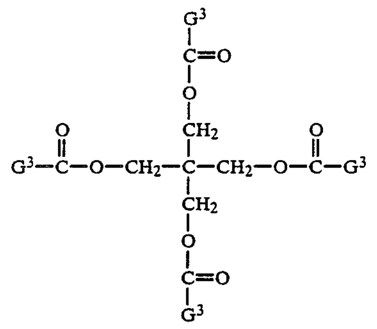 |
| where $G^3$ = | 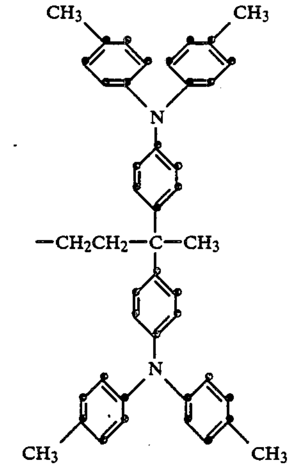 |

The cluster triarylamines of the present invention possess a high resistance to oxidation to form colored products when compared with compounds such as those generically described in Belgian Pat. No. 753,415. While the inventor does not wish to be bound by any explanation of the superior resistance of the present compounds to oxidation to colored products, it is theorized that the absence of a third aromatic ring on each carbon connecting each two triarylamine groups lends stability to the compounds; i.e. one does not have present the elements of a triphenylmethane leuco dye. The prior art compounds of U.S. Pat. No. 4,140,529 and Belgian Pat. No. 753,415 comprise a phenylene group connecting the two halves of the dimer, as can be seen in Reaction I (where R is another diarylmethane group). The phenylene group makes the prior-art compounds more susceptible to oxidation to form colored products because a positive charge formed can resonate (delocalize) into the phenyl ring, as well as into the two rings carrying nitrogen substituents.

Reaction I

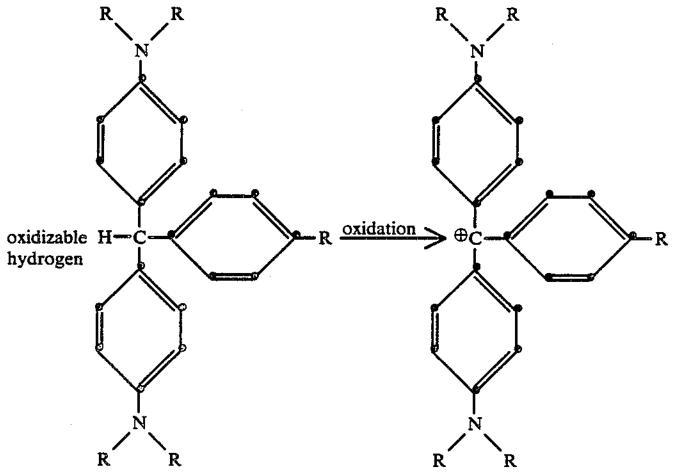

-continued

Reaction I

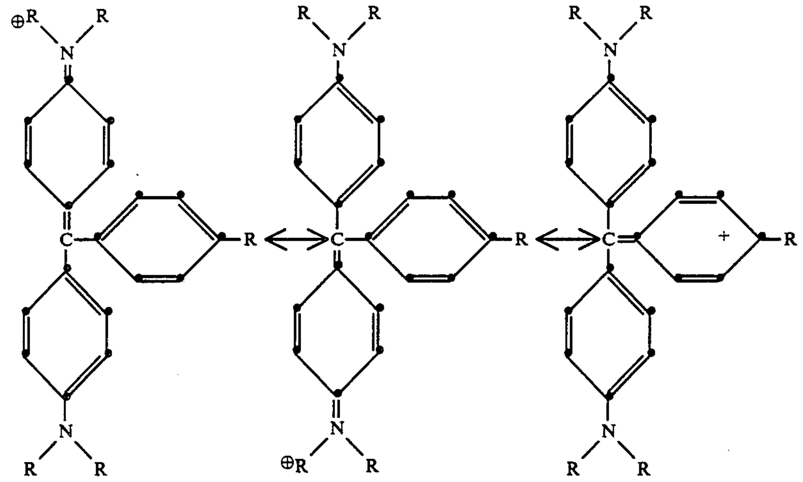

The compounds of this class are known as triphenylmethane dyes. In the compounds of the present invention there is either an aliphatic chain in place of the phenyl so that this resonance cannot occur (e.g. compound I, Table I) or the oxidation-sensitive hydrogen has been replaced by a methyl group that does not oxidize (e.g. compound IV,, Table I). This explains why, in the generic description of the present invention, $Q_4$ can only represent $CH_3$ (and not H) when x or z equals 1 or 2 and n is 0.

The cluster triarylamines of the present invention also possess unexpectedly high $T_g$. The importance of high $T_g$ has been recognized in the prior art. For example, U.S. Pat. No. 4,140,529 states that the $T_g$ of a charge-transport layer in a multilayer electrophotographic element has to be substantially higher than normal copier operating temperatures to allow efficient charge transport as well as providing resistance to impaction by dry developers and leaching of the active components from the binder material. Belgian Pat. No. 753,415 states that the compounds disclosed therein are thermally stable, however, it is referring to storage stability of elements containing the compound and not to their thermal stability during use in the copier.

However, there is a need for electrophotographic elements which are thermally stable at temperatures much higher than those encountered in many copier processes. An example of a high temperature process would be thermal transfer of toner images. When the high $T_g$ cluster triarylamines of the present invention make up a substantial proportion of an electrographic element, the overall $T_g$ of the element is increased. A high $T_g$ element can be used effectively in a thermal transfer process and in addition, the element retains its sensitivity at higher temperatures than a similar element with lower $T_g$.

The cluster triarylamines of this invention are particularly useful in electrophotographic elements. As such, compositions comprising the cluster triarylamines are applied as layers to electrically conductive substrates to form electrophotographic elements. For instance, the cluster triarylamines of this invention may be used in aggregate photoconductive compositions, homogeneous compositions and in both the charge-generation and charge-transport layers of multilayer electrophotographic elements.

Aggregate photoconductive compositions comprise an organic sensitizing dye and a polymeric material such as an electrically insulating film-forming polymeric material. They may be prepared by several techniques, now well known in the art. Examples of these techniques include the dye-first technique described in Gramza et al, U.S. Pat. No. 3,615,396 issued Oct. 26, 1971 and the shearing method described in Gramza, U.S. Pat. No. 3,615,415 issued Oct. 26, 1971.

By whatever method prepared, the aggregate composition is combined with one or more cluster triarylamines in a suitable solvent to form a composition which is coated on a suitable support to form a separately identifiable multiphase composition. The heterogeneous nature is generally apparent when viewed under magnification, although such compositions may appear to be substantially optically clear to the naked eye in the absence of magnification.

Electrophotographic elements of the invention containing the above-described aggregate photoconductive composition can contain a dispersion or solution of the photoconductive composition, followed by a coating or forming a layer on an electrically conductive substrate. Supplemental materials useful for changing the spectral sensitivity or electrophotosensitivity of the element can be added to the composition of the element when it is desirable to produce the characteristic effect of such materials. If desired, other polymers can be incorporated in the vehicle, for example to alter physical properties such as adhesion of the photoconductive layer to the support and the like.

In addition to electrophotographic elements containing the above-described aggregate photoconductive compositions there are other useful embodiments of the present invention. For example, homogeneous electrophotographic elements can be prepared with one or more cluster triarylamines of this invention in the usual manner. In other words, by blending a dispersion or solution of the cluster triarylamines together with sensitizing dye and binder, when necessary or desirable, and coating or forming a layer on an electrically conductive substrate. Organic photoconductors known in the art can be combined with the present cluster triarylamines. In addition, supplemental materials useful for changing the spectral sensitivity, or electrophotosensitivity, of the element can be added when it is desirable to produce the characteristic effect of such materials.

In addition to electrographic elements containing the above-described aggregate photoconductive compositions and homogeneous photoconductive compositions, the organic compounds of this invention may be used in multilayer electrophotographic elements. A multilayer electrophotographic element typically comprises an electrically conductive substrate, a charge-generation layer in electrical contact with the conductive substrate and a charge-transport layer in electrical contact with the charge-generation layer. The charge-generation layer, upon exposure to actinic radiation, is capable of generating and injecting charge into the charge-transport layer. The charge-transport layer accepts and transports the injected charge away from the charge-generation layer to the surface of the electrophotographic element, where it is neutralized.

Typically the charge-transport layer is substantially non-adsorbing in the spectral region of intended use, but is "active" in that it allows injection of photogenerated holes from the charge-generation layer and allows these holes to be transported therethrough. The charge-generation layer is a photoconductive layer which is capable of photogenerating and injecting photogenerated holes into the contiguous charge-transport layer. The organic compounds of this invention may be used in either the charge-generation layer or the charge-transport layer of a multilayer element.

Suitable substrates for electrophotographic elements of the invention include electrically conducting substrates such as paper or conventional substrates, for example, cellulose acetate, cellulose nitrate, polystyrene, poly(ethylene terephthalate), poly(vinyl acetate), polycarbonate and related substrates having a conductive layer thereon. A useful conductive substrate is prepared by coating a transparent film support material with a layer containing a semiconductor such as cuprous iodide dispersed in a resin. Suitable conducting coatings are also prepared from the sodium salt of a carboxyester lactone of maleic anhydride-vinyl acetate copolymer.

Additional useful conductive layers include carbon-containing layers such as conductive carbon particles dispersed in a resin binder. Metal coated papers; metal-paper laminates; metal foils such as aluminum foil; metal plates such as aluminum, copper, zinc, brass and galvanized plates; as well as vapor deposited metal layers such as silver, nickel or aluminum deposited on conventional film supports are also useful, as are conductive or conductor-coated glasses.

Sensitizing compounds, if desired for use with the photoconductive layers of the elements of the present invention, are selected from a wide variety of materials known in the art as sensitizers for organic photoconductors.

The amount of sensitizer that is added to a photoconductive composition of the invention to give effective increases in speed varies widely. The optimum concentration will vary with the sensitizing compound used. In general, substantial speed gains are obtained where an appropriate sensitizer is added in a concentration range from about 0.0001 to about 10 weight percent or more based on the weight of the coating composition. Normally, sensitizers are added to the coating composition in an amount of 0.005 to about 5.0 weight percent of the total coating composition.

The following procedures and examples are provided to illustrate the preparation and utility of organic compounds used in the present invention.

EXAMPLES

Comparison Compound A

A quantity of the compound listed in claim 3 of U.S. Pat. No. 4,140,529 was prepared by the procedure set forth in Example 2 of that reference. The compound, after five recrystallizations, was noted to be approximately 96% pure. The compound (which will be referred to as compound A) had a melting point of from 214° to 215.9° C. and a $T_g$ of 70° C.

The following examples illustrate the relative superiority of the $T_g$ of compounds of the present invention when compared with compound A.

EXAMPLE 1

Synthesis of Compound I

In a stoppered Erlenmeyer flask were mixed about 15 grams of a 50% solution in water of glutaraldehyde, and about 42.6 grams acetic anhydride. The mixture was stirred magnetically, overnight. The mixture was then diluted with about 400 mL acetic acid, and about 54.6 grams of 4,4-dimethyltriphenylamine, and about 2 grams of methanesulfonic acid were then added. The mixture was warmed gently and stirred overnight. A nodule formed and subsequently more dispersed solid formed. The powder and the nodule were filtered off and were stirred and warmed in about 500 mL of 20% toluene in acetic acid. The nodule disintegrated to give a suspended powder. The mixture was cooled and the powder was filtered off and recrystallized twice from toluene-ethanol. The white solid had m.p. 257° C. and $T_g$ 108° C. Mass spectrometry showed essentially only the desired compound with m/e 1156. Quantitative HPLC showed the produce to be of high purity.

EXAMPLE 2

Synthesis of Compound II

In a stoppered Erlenmeyer flask a mixture of about 4 grams of a 50% solution in water of glutaraldehyde and about 11.36 grams of acetic anhydride, was stirred magnetically for two hours, with mild warming, and then homogenized. To the mixture were added about 80 mL of acetic acid and about 23.4 grams of 3,4',4"-trimethyltriphenylamine, and about 0.8 grams of methane sulfonic acid. The mixture was stirred magnetically at about 50° C. Solid began to go into solution but quite soon a thick paste became suspended in ropy clots in the solvent. The mixture was warmed and stirred overnight in which time the paste became a hard crystalline mass. The mass was crushed under the solvent and was filtered off, and rinsed with a small quantity of acetic acid. The solid was recrystallized three times from toluene-ethanol. The product was homogeneous as indicated by thin-layer chromatography (silica gel 60 plate, 30% toluene in cyclohexane).

The white solid had a $T_g$ of 114° C. The m.p. was ill-defined but mass spectrometry showed that the product was the desired one, m/e 1212 and quantitative HPLC showed it to be 99.5 area % pure.

EXAMPLE 3

Synthesis of Compound III

In a stoppered Erlenmeyer flask was placed a mixture of about 11.48 grams of 3,4',4''-trimethyltriphenylamine, about 70 mL of acetic acid and about 0.86 grams of succinaldehyde bis(sodium bisulfite) complex. The mixture was warmed to 40° C. and stirred magnetically, and about 10 mL of methanesulfonic acid, and an additional 10 mL of acetic acid added. Solids went into solution and a hard nodule formed which was broken up. More succinaldehyde complex was added, to give a total of 2.94 grams, and another 5 mL methanesulfonic acid were added. The mixture was stirred at 40° C. overnight.

The solid was filtered off, dissolved in warm toluene and washed with warm 10% NaOH solution. The toluene layer was dried ($Na_2CO_3$), filtered and evaporated down. The residue was recrystallized five times from toluene. The white solid had m.p. 326° C. and $T_g$ 135° C. A mass spectrum showed m/e 599, M++ for the desired compound. Quantitative HPLC showed the product to b 99.8 area % pure.

EXAMPLE 4

Synthesis of Compound IV

In a stoppered Erlenmeyer flask was placed a mixture of about 2.66 grams of 4,4'-diacetylbibenzyl, about 10.92 grams of 4,4'-dimethyltriphenylamine, about 30 mL of acetic acid, and about 1 mL methanesulfonic acid. The mixture was heated at about 70° C. with magnetic stirring, for one week, during which time another 1 mL methanesulfonic acid was added.

The reaction mixture was chilled and the solid that had come down was filtered off, dissolved in toluene, treated with solid sodium carbonate, filtered and recovered by evaporation. The crude solid was chromatographed over a column of silica gel, (230–400 mesh), at 70 lbs/in$^2$ pressure starting with 10% dichloromethane in cyclohexane, and gradually increasing the percentage of dichloromethane.

Starting, 4,4'-dimethyltriphenylamine eluted first. The second component to come off was identified by mass spectrometry as the desired product m/e 1322, M+. This product was recrystallized three times from toluene-ethanol. The white solid had m.p. 323° C. and $T_g$ 131° C.

EXAMPLE 5

Preparation of 4,4-bis[4-(4,4'-ditolylamino)phenyl]pentanoic acid

Into a 1 L Erlenmeyer flask were placed about 225 grams (0.824M) of 4,4'-dimethyltriphenylamine (I), about 46 grams (0.397M) of levulinic acid (II), about 370 grams (3.85M) of practical grade methanesulfonic acid and about 9 grams (0.05M) of methanesulfonic anhydride. The mixture was stirred until all of the solids had dissolved. The flask was capped with a cork in order to prevent admission of excess atmospheric moisture and left at room temperature.

After 12 days, the resulting viscous reaction mixture was poured slowly into 4 L of water using rapid stirring to break up the solids as they formed. The solids were collected by filtration and placed into an additional 4 L of water and leached under agitation. The solids were recollected by filtration, dissolved in a toluene/dichloromethane mixture (500 mL at ¼ ratio), and extracted with three 600 mL portions of water. Additional dichloromethane was added as needed. The organic solvents were evaporated and the resulting solid was leached with cyclohexane. The cyclohexane was poured onto a short column of silica gel and eluted with dichloromethane until all of the unreacted 4,4'-dimethyltriphenylamine was removed. The column was then eluted using 1/1 toluene/acetonitrile and the latter solvents were collected and evaporated. The resulting solids were added to the cyclohexane insoluble solids. The latter were then dissolved in dichloromethane and placed atop a new silica gel column. The colored materials were eluted using $CH_2Cl_2$. The column was then eluted with 1/1/toluene/acetonitrile. The solvents were collected and evaporated and the residue was recrystallized using 2 L of 10/1 acetonitrile/toluene.

Yield: 183 gm, 71%, m/e 644, m.p. 193°–194° C. Analysis: Calcd. for $C_{45}H_{44}N_2O_2$: C, 83.9; H, 7.0; N, 4.3%. Found: C, 83,9, H, 6.9; N, 4.3.

EXAMPLE 6

Preparation of 4,4-bis[4-(4,4'-ditolylamino)phenyl]-1-pentanol

A suspension of about 40 grams 4,4-bis[4-(4,4'-ditolylamino)phenyl]pentanoic acid, in about 300 mL of toluene was cautiously treated with stirring with VITRIDE®, (70% sodium bis(2-methoxyethoxy)aluminum hydride in toluene), until foaming ceased, and then a small excess was added. When TLC (silica gel plate, 10% ethyl acetate in toluene) showed complete disappearance of starting acid and formation of a clean product spot the excess VITRIDE® was decomposed by careful addition of 10% sodium hydroxide solution, and then 250 mL more of the latter solution were added. The product was isolated by separation of the toluene layer, with conventional methods following. The crude solid product was recrystallized from ethanol containing a small amount of ethyl acetate. When the solution was cooled slowly, with stirring and seeding, very fine crystals came out of solution slowly. The dried white solid showed no I.R. carbonyl absorption at 1710 cm$^{-1}$. A mass spectrum showed m/e 630, M for the desired alcohol.

EXAMPLE 7

Preparation of Compound VI

To a solution of about 12.6 grams 4,4-bis[4-(4,4'-ditolylamino)phenyl]-1-pentanol, in 110 mL of dry dichloromethane containing about 3 grams of triethylamine was added about 1.76 grams of 1,3,5-benzenetricarboxylic acid chloride with swirling. TLC (silica gel plate; toluene) later showed a sequence of three product spots. The reaction mixture was washed with dilute HCl and worked up in the usual way. The crude product was chromatographed over neutral alumina, Brockmann activity grade 1, using 50% $CH_2Cl_2$ in cyclohexane. The first product fraction to come off was examined by field desorption mass spectrometry and showed only m/e 2046, M for the desired triester. A portion of this product was purified further by flash chromatography over silica by the method of Still, starting with 50% toluene in cyclohexane and gradually increasing the toluene content. The homogeneous fractions were identified by TLC, combined and evaporated down. Treatment with a little acetonitrile gave a hard solid which was crushed and dried. An I.R. spectrum showed a carbonyl absorption at 1740 cm$^{-1}$. Thermal analysis gave $T_g$ 120° C. Quantitative HPLC showed a purity of 99.4 area %.

Compound V was prepared by similar techniques as described in Examples 5-7.

EXAMPLE 8

Preparation of Compound IX

A mixture of about 24.64 grams of 4,4-bis[4-(4,4'-ditolylamino)phenyl]pentanoic acid and about 1.08 grams of pentaerythritol was dissolved by warming in about 60 mL pyridine. The solution was cooled to 0° C. and treated with about 21.6 grams dicyclohexylcarbodiimide. The mixture was allowed to stand in a refrigerator for several days and was then diluted with dichloromethane and extracted with an excess of 10% HCl solution. The mixture had to be filtered through a sintered-glass funnel to remove some insoluble material. The organic layer was washed with sodium bicarbonate solution, separated, ddried ($MgSO_4$), filtered and evaporated down. A portion of the crude residue was chromatographed over fluorescent silica in a quartz column, using 20% dichloromethane in cyclohexane, and scanning with a short-wave-length U.V. lamp. The fractions containing the first component to come off where checked by TLC (silica gel plate; 85% dichloromethane in cyclohexane), combined and evaporated down. The residual product showed a sharp singlet at 1750 waves/cm in the infrared. The product was further purified by flash chromatography by the method of Still, over silica using 40-55% dichloromethane in cyclohexane. Those fractions homogeneous by TLC were combined and evaporated down to a dry crushable glass. Mass spectrometry on the product showed only m/e 2640, M for the desired tetra-ester. Quantitative HPLC showed the product to be greater than 97 area % pure. Thermal analysis showed the product to have $T_g$ 93° C.

Compounds VII and VIII were prepared by similar techniques using the appropriate hydroxyl containing materials in place of pentaerythritol of this example.

The Tg of the the compounds were tested by differential scanning calorimetry (DSC). The samples were characterized using a DuPont 990 thermal analyzer equipped with a 960 module cell base and DSC cell. They were heated at 10 deg C/min in a nitrogen atmosphere. The glass transition temperature, Tg, is defined as the mid-point of the heat capacity (delta $C_p$) shift. The range extends from the onset of the break in delta $C_p$ to where it stabilizes. The results are listed in table II below.

TABLE II

| Compound/No. from Table I | $T_g$ (°C.) |
|---|---|
| A (Control) | 70 |
| I | 107-108 |
| II | 114 |
| III | 135 |
| IV | 131 |
| V | 91 |
| VI | 120 |
| VII | 114 |
| VIII | 120 |
| IX | 113 |

The above results demonstrate the superiority of the $T_g$ of the compounds of the present invention over a prior art compound.

EXAMPLE 9

A comparison was made of multilayer electrophotographic elements having charge-transport layers comprising either a cluster triarylamine of the present invention (compound I from Table I) or a prior art charge-transport material. The cluster triarylamine (40%) was mixed with a polyester binder (60%) prepared from 4,4'(2-norbornylidene)diphenol, 40 mol percent azelaic acid and 60 mol percent terephthalic acid. The compound was coated as a charge-transport layer over an aggregate charge-generation layer containing 1,1-Bis(4-di-p-tolylaminophenyl)cyclohexane (See U.S. Pat. No. 4,127,412, Col. 5, lines 51-54.)

A control was prepared in accordance with Example 1 of U.S. Pat. No. 4,175,960 utilizing nickel coated polyethylene terephthalate as the conductive support.

The following monochromatic photodecay data for discharge from −500 V to −100 V by 680 nm light were obtained.

TABLE III

| Element | Relative Speed (ergs/$cm^2$) |
|---|---|
| Control | 1* |
| High Tg element | 1.16 |

*Control arbitrarily assigned a value of 1.0 for ease of comparison.

The above results demonstrate that a cluster triarylamine of the present invention, when used as a charge-transport layer in a multilayer electrophotographic element, possesses sensitometric properties that are substantially similar to the control element.

EXAMPLE 10

Figure 2:
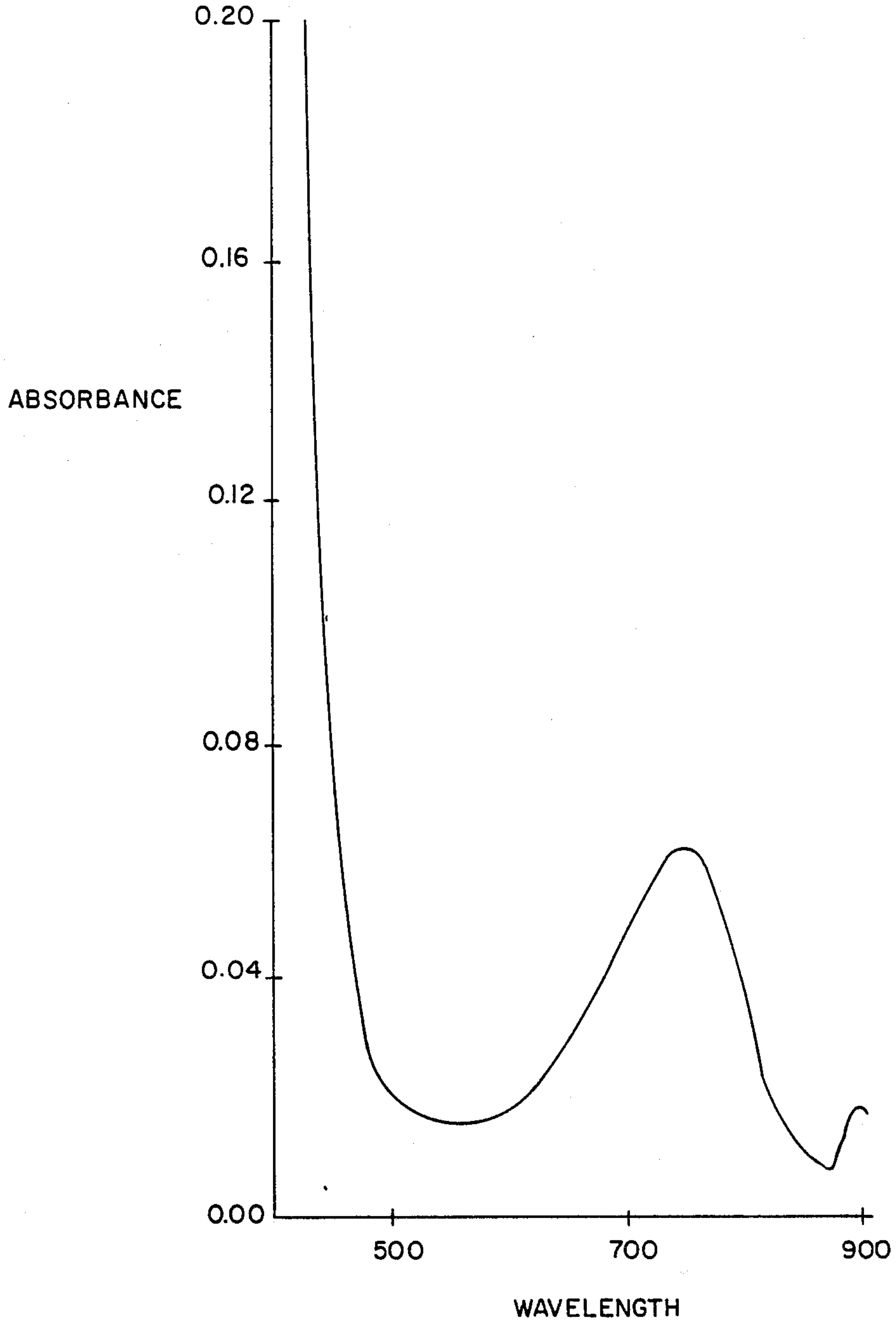
FIGS. 2 and 3 are absorption curves for compounds outside the scope of the invention having the xylylidene linkage suggested by the prior art, which have been subjected to accelerated oxidation tests for comparison with compounds of the invention.
Figure 3:
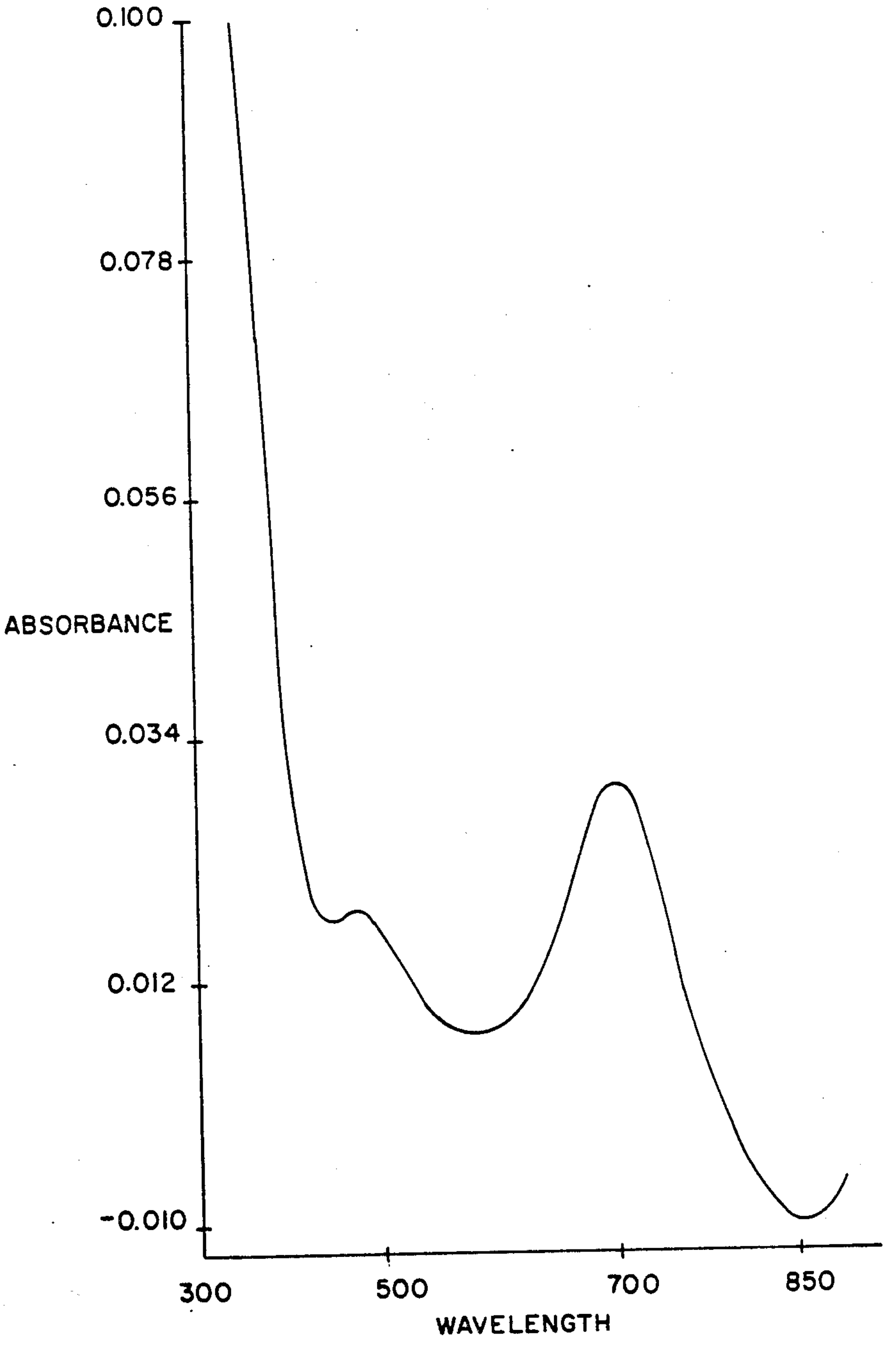

The following example demonstrates the superior oxidation resistance of a compound of the present invention when compared with prior art compounds. An accelerated spot test to demonstrate the relative stability of these compounds was conducted. The compound to be tested was dissolved in acetonitrile in a spectrophotometric cell. A small amount (0.02 to 0.1 mL) of a $10^{-2}$M ceric solution (ceric ammonium sulfate) was injected into the stoppered cell which was then shaken. The spectrophotometric characteristics of the materials were immediately tested. The results of the spectrophotometric tests are shown in FIGS. 1-3. FIG. 1 shows a spectrophotometric analysis performed on Compound II from Table I after the accelerated spot test. As can be seen from FIG. 1, Compound II exhibited no absorption maximum in the visible region. The prior art compounds used for comparison were of the type generically described in Belgian Pat. No. 753,415.

Comparison compound B is

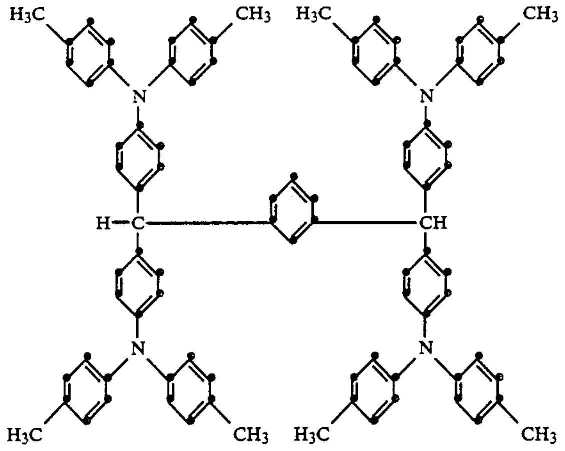

Comparison compound C is:

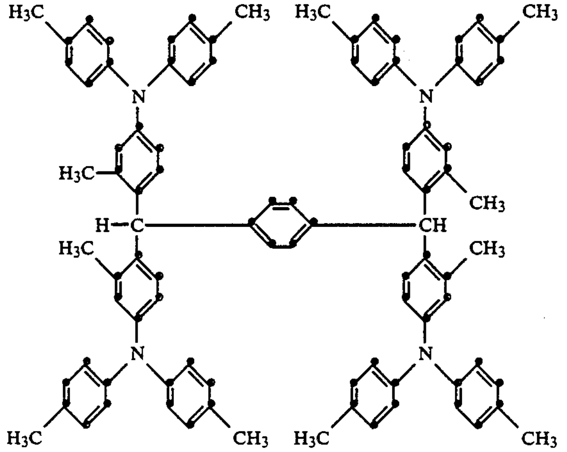

As can be seen from FIGS. 2 and 3 the prior art compounds exhibited substantial absorption maxima in the visible light region. The above tests demonstrate that a cluster triarylamine compound of the present invention possesses a higher resistance to oxidation, and therefore a lower propensity for color formation.

The invention has been described in detail with particular reference to preferred embodiments thereof, but it will be understood that variations and modifications can be effected within the spirit and scope of the invention.

We claim:

1. An organic compound having the formula selected from the group consisting of:

(a)

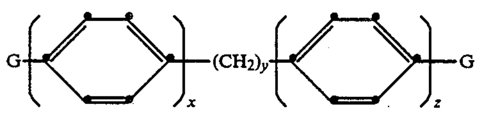

wherein x is an integer from 0 to 2, y is an integer from 1 to 6, and z is an integer from 0 to 2;

(b)

$$(G-O-\overset{\overset{O}{\|}}{C}-)_a\ L;\ \text{and}$$

-continued (c)

$$(G-\overset{\overset{O}{\|}}{C}-O-)_a\ L$$

wherein L is aliphatic, alicyclic or aromatic and a is an integer from 2 to 6; and wherein G has the formula

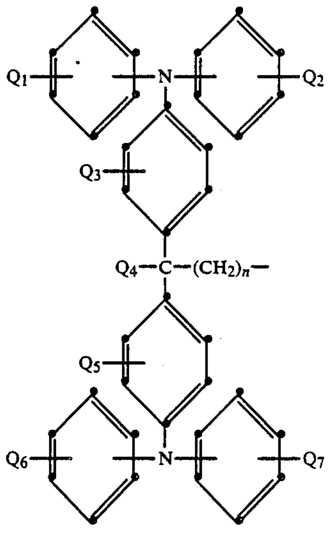

wherein n is an integer from 0 to 6; $Q_1$, $Q_2$, $Q_3$, $Q_5$, $Q_6$, $Q_7$, which may be the same or different, represent H or $CH_3$, and $Q_4$ represents H or $CH_3$ when x and z are 0 or n is greater than 0, or $Q_4$ represents $CH_3$ when x or z are 1 or 2 and n is 0.

2. An organic compound having a formula selected from Table I.

3. An organic compound having the formula

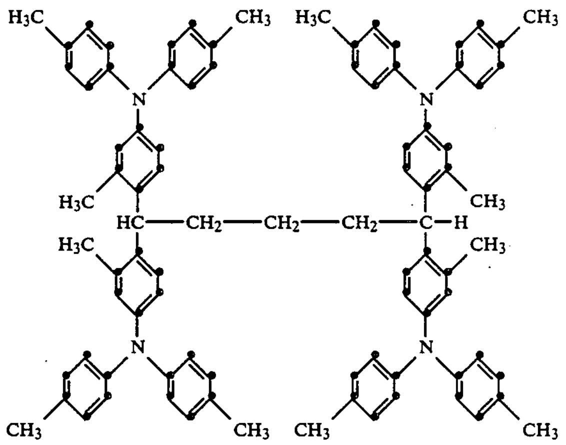

4. An electrophotographic element comprising:
(a) an electrically conductive substrate, and
(b) a layer comprising an organic compound as described in claim 1.

5. In an electrophotographic element comprising:
(a) an electrically conductive substrate,
(b) a charge-generation layer in electrical contact with said substrate, and
(c) a charge-transport layer in electrical contact with said charge-generation layer, (i) said charge-generation layer, upon exposure to actinic radiation, being capable of generating and injecting charge into said charge-transport layer, and (ii) said charge-transport layer comprising a charge-transport material capable of accepting and transporting injected charge from said charge-generation layer, the improvement wherein said charge-transport material comprises an organic compound as described in claim 1.

6. In an electrophotographic element comprising:

(a) an electrically conductive substrate, (b) a charge-generation layer in electrical contact with said substrate, and (c) a charge-transport layer in electrical contact with said charge-generation layer, (i) said charge-generation layer, upon exposure to actinic radiation, capable of generating and injecting charge into said charge-transport layer, and (ii) said charge-transport layer capable of accepting and transporting injected charge from said charge-generation layer, the improvement wherein said charge-generation layer comprises an organic compound as described in claim 1.

7. An electrophotographic element comprising:

(a) an electrically conductive substrate, and (b) a photoconductive layer in electrical contact with said substrate, said photoconductive layer comprising an organic compound as described in claim 1.

8. A process for forming a visible image on an electrophotographic element described in claim 4 said process comprising the steps of electrically charging a surface of said electrophotographic element, exposing said charged surface to actinic radiation to form an electrostatic latent image, and developing said latent image to form a visible image.

* * * * *